United States Patent
Kawazoe et al.

(10) Patent No.: US 7,982,049 B2
(45) Date of Patent: *Jul. 19, 2011

(54) α-FORM OR β-FORM CRYSTAL OF ACETANILIDE DERIVATIVE (75) Inventors: Souichirou Kawazoe, Takahagi (JP); Kenichirou Sakamoto, Takahagi (JP); Yuji Awamura, Tsukuba (JP); Tatsuya Maruyama, Tsukuba (JP); Takayuki Suzuki, Tsukuba (JP); Kenichi Onda, Tsukuba (JP); Toshiyuki Takasu, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 708 days.

This patent is subject to a terminal disclaimer.

(21) Appl. No.: 12/007,653

(22) Filed: Jan. 14, 2008

(65) Prior Publication Data

US 2008/0214633 A1    Sep. 4, 2008

Related U.S. Application Data (63) Continuation of application No. 10/494,018, filed on Apr. 29, 2004, now Pat. No. 7,342,117.

(30) Foreign Application Priority Data

Oct. 30, 2001 (JP) ................................. 2001-332914

(51) Int. Cl.
*A61K 31/426* (2006.01)
*C07D 277/40* (2006.01)

(52) U.S. Cl. ........................................ 548/194; 514/370

(58) Field of Classification Search ................... 548/194
See application file for complete search history.

(56) References Cited

U.S. PATENT DOCUMENTS

| 6,346,532 | B1 | 2/2002 | Maruyama et al. |
| 6,627,642 | B1 | 9/2003 | Kimura et al. |
| 6,706,733 | B2 | 3/2004 | Kimura et al. |
| 7,342,117 | B2 * | 3/2008 | Kawazoe et al. ............. 548/194 |

FOREIGN PATENT DOCUMENTS

| EP | 466952 A | 1/1992 |
| JP | 11-255649 | 9/1999 |
| JP | 2000-212168 | 8/2000 |
| WO | WO-99/20607 A1 | 4/1999 |

OTHER PUBLICATIONS

International Search Report, for PCT/JP02/11217, dated Jan. 28, 2003.
Rouhi, Chemical and Engineering News, Feb. 24, 2003, pp. 32-35, especially p. 32.

* cited by examiner

*Primary Examiner* — Laura L. Stockton
(74) *Attorney, Agent, or Firm* — Finnegan, Henderson, Farabow, Garrett & Dunner, LLP

(57) ABSTRACT

To provide novel crystals useful as an ingredient for the production of a diabetes remedy. The invention is concerned with α-form crystal and β-form crystal of (R)-2-(2-aminothiazol-4-yl)-4'-[2-[(2-hydroxy-2-phenylethyl)amino]ethyl]acetanilide. The α-form crystal does not exhibit hygroscopicity and has stability such that it can be used as a medicine, and is useful for mass synthesis in the industrial production. The β-form crystal does not relatively exhibit hygroscopicity and is also useful as a production intermediate of the α-form crystal.

16 Claims, 9 Drawing Sheets

α-FORM OR β-FORM CRYSTAL OF ACETANILIDE DERIVATIVE

This is a continuation of application Ser. No. 10/494,018, now U.S. Pat. No. 7,342,117, filed Apr. 29, 2004 and claims the benefit of PCT/JP02/11217 filed Oct. 20, 2002, all of which are incorporated herein by reference.

TECHNICAL FIELD

The present invention relates to an α-form crystal or β-form crystal of (R)-2-(2-aminothiazol-4-yl)-4'-[2-[(2-hydroxy-2-phenylethyl)amino]ethyl]-acetanilide which is useful as a diabetes remedy and to a drug containing the same, especially a diabetes remedy.

BACKGROUND ART

The present inventors have reported that (R)-2-(2-aminothiazol-4-yl)-4'-[2-[(2-hydroxy-2-phenylethyl)amino]ethyl]-acetanilide dihydrochloride represented by the following chemical structural formula has both an insulin secretion promoting action and an insulin sensitivity potentiating action, further has anti-obesity and anti-hyperlipemia actions due to a selective stimulating action to $\beta_3$-receptors and is a useful compound for remedy of diabetes (WO 99/20607, Example 41).

However, since this dihydrochloride has strong hygroscopicity and is unstable, its use as a medicine was still problematic.

Medicines are required to be stable against humidity, temperature, light, and the like over a long period of time and also to have stability in the formulation step. If medicines have strong hygroscopicity, they physically and chemically change or cause such an inconvenience that the water content is different depending upon lots. Accordingly, it is necessary to always store them in a drying chamber or to provide a drying step, which is not preferable from the standpoint of industrial use.

DISCLOSURE OF THE INVENTION

Under such technical circumstances, the present inventors have made extensive and intensive investigations about the foregoing compound described in Example 41 of WO 99/20607 and found novel α-form crystal (hereinafter simply referred to as "α-form crystal") and β-form crystal (hereinafter simply referred to as "β-form crystal") of (R)-2-(2-aminothiazol-4-yl)-4'-[2-[(2-hydroxy-2-phenylethyl)amino]ethyl]acetanilide. Both of these two novel crystals are of a free base and are distinguished from each other by powder X-ray diffraction spectrum and DSC analysis. The previously obtained dihydrochloride crystal was a strongly hygroscopic and unstable crystal such that it exhibits a rapid increase in hygroscopicity from a relative humidity of 80% and holds moisture of about 14% at a relative humidity of 90%.

In contrast, the "α-form crystal" of the invention has a moisture-holding amount of not more than 0.2% over the entire range of relative humidity from 5% to 95%, is a stable crystal not exhibiting hygroscopicity, and is suitable for use as a medicine. Further, in the "β-form crystal", an increase in the weight is observed from a relative humidity of about 20%, and it holds moisture of about 3% and has weak hygroscopicity. However, this crystal is a metastable-form crystal and can be used as a medicine. Also, the "β-form crystal" is useful as a production intermediate of the "α-form crystal".

Each of the α-form crystal and the β-form crystal is characterized by the following crystal lattice spacings [2θ(°)] of powder X-ray diffraction spectrum and heat absorption peak of DSC analysis. Incidentally, with respect to the powder X-ray diffraction, in determining the identity of crystal, crystal lattice spacings and an overall pattern are important in the nature of data. On the other hand, since a relative intensity can vary a little depending upon the direction of crystal growth, particle size and measurement condition, it should not be strictly interpreted.

TABLE 1

(α-Form Crystal)

| Crystal lattice spacing | Relative intensity |
|---|---|
| 5.32 | Strong |
| 8.08 | Strong |
| 15.28 | Slightly strong |
| 17.88 | Slightly strong |
| 19.04 | Slightly strong |
| 20.20 | Slightly strong |
| 23.16 | Slightly strong |
| 24.34 | Slightly strong |

TABLE 2

(β-Form Crystal)

| Crystal lattice spacing | Relative intensity |
|---|---|
| 9.68 | Medium |
| 19.76 | Slightly strong |
| 20.72 | Medium |
| 22.10 | Medium |
| 23.52 | Medium |

Also, in the DSC analysis, the α-form crystal had a heat absorption peak at 142 to 146° C., and the β-form crystal had heat absorption peaks at 90 to 110° C. and at 142 to 146° C., respectively.

The measurement of the powder X-ray diffraction was carried out using MAC Science MXP18TAHF22 under the following conditions. Tube: Cu, tube current: 40 mA, tube voltage: 40 kV, sampling width: 0.020°, scanning rate: 3°/min, wavelength: 1.54056 angstrom, measurement diffraction angle range (2θ): 5 to 40°.

Thermal analyses (DSC and TGA) were respectively carried out under the following conditions.

DSC: Perkin-Elmer Pyris 1, from 25° C. to 250° C. (10° C./min), $N_2$ (20 mL/min), aluminum-made sample pan. TGA:

Perkin-Elmer TGA 7, from 25° C. to 250° C. (10° C./min), $N_2$ (20 mL/min), platinum-made sample pan.

Nuclear magnetic resonance (NMR) spectra were measured using JEOL JNM-LA400 and JEOL JNM-A500, and tetramethylsilane (TMS) was used as an internal standard.

Mass analysis spectra were measured using JEOL DX-300 and JEOL LX-2000.

Further, the invention relates to a drug containing the α-form crystal or β-form crystal of (R)-2-(2-aminothiazol-4-yl)-4'-[2-[(2-hydroxy-2-phenylethyl)amino]-ethyl]-acetanilide, especially a diabetes remedy having both an anti-obesity action and an anti-hyperlipemia action.

Administration of a drug containing the crystal of the invention as a starting material for the production of medicines may be either oral administration by, for example, tablet, pill, capsule, granule, or powder, or parenteral administration by, for example, inhaling agent. Examples of the solid composition for oral administration include tables, powders, and granules. In such a solid composition, one or more active substances are mixed with at least one inert excipient such as lactose, mannitol, glucose, hydroxypropyl cellulose, microcrystalline cellulose, starch, polyvinylpyrrolidone, and magnesium metasilicate aluminate. The composition may also contain inert additives such as lubricants such as magnesium stearate; disintegrants such as carboxylmethyl starch sodium; and auxiliary solubilizers according to customary manners. If desired, tablets or pills may be coated with sugar coat or with gastric or enteric coating agents. The dose may be appropriately decided depending upon each particular case while taking into consideration of symptom, age, sex, etc. of the subject to be administered but is usually from about 0.01 mg/kg to 100 mg/kg per day for an adult in the case of oral administration, and that is administered at a time or by dividing into 2 to 4 times.

(Production Method)

The α-form crystal can be obtained by adding a recrystallization solvent (37% to 50% ethanol aqueous solution) to the β-form crystal of (R)-2-(2-aminothiazol-4-yl)-4'-[2-[(2-hydroxy-2-phenylethyl)amino]ethyl]-acetanilide, dissolving the β-form crystal by heating at about 70 to 80° C., and then gradually cooling the solution at a rate of about 10° C. per hour. Though the α-form crystal is likely crystallized in the large-scale production in the industrial production, it can be preferentially crystallized upon seeding with the α-form crystal.

The β-form crystal can be obtained by adding 1-(3-dimethylaminopropyl)-3-ethylcarbodiimide monohydrochloride to a mixed solution of (R)-2-[[2-(4-aminophenyl)ethyl]amino]-1-phenylethanol monohydrochloride, 2-aminothiazol-4-yl-acetic acid, concentrated hydrochloric acid and water at room temperature and neutralizing the resulting acidic solution to form a wet cake of the β-form crystal. (The wet cake as referred to herein means the state where the crystal is wetted by the solvent.)

Also, the β-form crystal can be obtained by adding a recrystallization solvent (37% to 50% ethanol aqueous solution) to the present β-form crystal, dissolving the β-form crystal by heating at about 70 to 80° C., and after setting up an external temperature at 20° C., rapidly cooling the solution. Also, the β-form crystal can be preferentially crystallized upon seeding with the β-form crystal.

As described previously, since the isolated β-form crystal can be again converted into the α-form after dissolution by heating, the β-form crystal is useful as a production intermediate of the α-form crystal.

BEST MODE FOR CARRYING OUT THE INVENTION

The invention will be specifically described below with reference to Examples 1 to 4, but it should not be construed that the scope of the invention is limited thereto. Since the starting compound was produced by a different method from that described in WO 99/20607, it will be described as Referential Examples 1 to 3. The synthesis routes of Referential Examples 1 to 3 and Examples 1 to 4 are illustrated below. Further, the production method of a crystal of (R)-2-(2-aminothiazol-4-yl)-4'-[2-[(2-hydroxy-2-phenylethyl)amino] ethyl]-etanilide dihydrochloride will be described as Comparative Referential Example.

Synthesis Route:

Hydrochloride or 1/2-sulfate

Hydrochloride

REFERENTIAL EXAMPLE 1

To a mixture of 5.90 kg of 4-nitrophenylethylamine monohydrochloride, 4.43 kg of (R)-mandelic acid, 2.94 kg of triethylamine and 22 L of N,N-dimethylformamide, 3.93 kg of hydroxybenztriazole and 5.58 kg of 1-(3-dimethylaminopropyl)-3-ethylcarbodiimide monohydrochloride (EDC) were added, and the mixture was stirred at around room temperature for 2 hours. 0.28 kg of EDC was further added, and the mixture was stirred at around room temperature overnight. The reaction solution was diluted with 110 L of water and extracted with ethyl acetate (60 L and 30 L). The organic layer was washed successively with 60 L of a 1M hydrochloric acid aqueous solution, 60 L of a 20% potassium carbonate aqueous solution and water (60 L and 60 L), and then concentrated in vacuo at 10 to 19° C. The residue was dissolved in 35 L of toluene by heating (at 87° C.), cooled, and then stirred at 20° C. overnight. A formed crystal was collected by filtration and washed with 10 L of toluene, followed by drying in vacuo. There was thus obtained 7.66 kg of (R)-2-hydroxy-N-[2-(4-nitrophenyl)ethyl]-2-phenylacetamide as a pale yellow crystal.

$^1$H-NMR (DMSO-$d_6$, 400 MHz) δ (ppm)=2.87 (2H, t, J=7.2 Hz), 3.30 to 3.46 (2H, m), 4.85 (1H, d, J=4.8 Hz), 6.12 (1H, d, J=4.8 Hz), 7.20 to 7.33 (5H, m), 7.40 (2H, d, J=8.0 Hz), 8.04 to 8.12 (3H, m). FAB-MS m/z: 301 (M+H)$^+$.

(Another Method) Production Method Using 4-nitrophenylethylamine 1/2 Sulfate:

To a mixture of 9.77 g of 4-nitrophenylethylamine 1/2 sulfate, 6.00 g of (R)-mandelic acid, 4.70 g of potassium carbonate and 60 mL of N,N-dimethylformamide, 6.14 g of hydroxybenztriazole and 8.70 g of 1-(3-dimethylaminopropyl)-3-ethylcarbodiimide monohydrochloride (EDC) were added, and the mixture was stirred at around room temperature for 2 hours. 0.87 g of EDC was further added, and the mixture was stirred at around room temperature overnight. The reaction solution was diluted with water and extracted with ethyl acetate. The organic layer was washed successively with 1M hydrochloric acid aqueous solution, 20% potassium carbonate aqueous solution and water, and then concentrated in vacuo. The residue was recrystallized from toluene to obtain 10.4 g of (R)-2-hydroxy-N-[2-(4-nitrophenyl)ethyl]-2-phenylacetamide as a pale yellow crystal.

REFERENTIAL EXAMPLE 2

A mixture of 7.51 kg of (R)-2-hydroxy-N-[2-(4-nitrophenyl)ethyl]-2-phenylacetamide, 23 L of 1,3-dimethyl-2-imidazolidinone and 23 L of tetrahydrofuran was cooled to −18° C., to which was then dropped 49.4 kg of 1M borane-tetrahydrofuran solution at not higher than −7° C. Thereafter, the temperature was increased to 70° C., and the mixture was stirred for 5 hours. The reaction mixture was cooled to −12° C., to which were then added 2.9 kg of methanol and 5.9 kg of concentrated hydrochloric acid at not higher than 5° C. The mixture was stirred at 68° C. for one hour and concentrated in vacuo such that the inner volume became 50 L. 60 kg of 30% $K_2CO_3$ aqueous solution and 6 L of water were added, and the mixture was extracted with 75 L of ethyl acetate. The organic layer was washed with 75 L and concentrated in vacuo. The residue was added with and dissolved in 75 L of isopropanol at 40° C., and the solution was crystallized from 2.46 kg of concentrated hydrochloric acid, followed by stirring at 23° C. overnight. A crystal was collected by filtration and washed with 38 L of isopropanol, followed by drying in vacuo. There was thus obtained 7.29 kg of (R)-2-[[2-(4-nitrophenyl)-ethyl] amino]-1-phenylethanol monohydrochloride.

$^1$H-NMR (DMSO-$d_6$, 400 MHz) δ (ppm)=3.00 to 3.08 (1H, m), 3.15 to 3.30 (5H, m), 5.00 to 5.05 (1H, m), 6.23 (1H, d, J=4.0 Hz), 7.29 to 7.35 (1H, m), 7.36 to 7.43 (4H, m), 7.57 (2H, d, J=8.4 Hz), 8.21 (2H, d, J=8.4 Hz), 9.12 (2H, br) FAB-MS m/z: 287 (M+H)$^+$.

REFERENTIAL EXAMPLE 3

A mixture of 11.0 kg of (R)-2-[[2-(4-nitrophenyl)-ethyl] amino]-1-phenylethanol monohydrochloride, 110 L of methanol and 1.20 kg of wet 10% palladium-carbon (wetting rate: 54.2%) was stirred under a hydrogen atmosphere until absorption of hydrogen stopped. The reaction solution was filtered, and the filtrate was concentrated in vacuo. The residue was added with and dissolved in 40 L of methanol at 40° C., and the solution was crystallized from 220 L of diisopropyl ether, followed by stirring at 20° C. overnight. A crystal was collected by filtration and washed with 30 L of diisopropyl ether, followed by drying in vacuo. There was thus obtained 9.43 kg of (R)-2-[[2-(4-aminophenyl)ethyl]-amino]-1-phenylethanol monohydrochloride.
(Another Method) Method of Using Ethyl Acetate as Crystallization Solvent:

A mixture of 15.0 g of (R)-2-[[2-(4-nitrophenyl)-ethyl] amino]-1-phenylethanol monohydrochloride, 90 mL of methanol and 655 mg of wet 10% palladium-carbon (wetting rate: 54.2%) was stirred under a hydrogen atmosphere until absorption of hydrogen stopped. The reaction solution was filtered. The filtrate was heated, to which was then intermittently added ethyl acetate while concentrating the methanol solution by heating, to form a slurry. A generated crystal was collected by filtration and washed with ethyl acetate, followed by drying in vacuo. There was thus obtained 12.9 g of (R)-2-[[2-(4-aminophenyl)ethyl]-amino]-1-phenylethanol monohydrochloride.

$^1$H-NMR (DMSO-$d_6$, 400 MHz) δ (ppm)=2.76 to 2.90 (2H, m), 2.95 to 3.16 (4H, m), 4.95 to 5.11 (3H, m), 6.20 (1H, d, J=4.0 Hz), 6.53 (2H, d, J=8.4 Hz), 6.89 (2H, d, J=8.4 Hz), 7.28 to 7.43 (5H, m), 8.97 (1H, br), 9.29 (1H, br.). FAB-MS m/z: 257 (M+H)$^+$.

EXAMPLE 1

Production of the β-form Crystal

To a mixed solution of 8.00 g of (R)-2-[[2-(4-aminophenyl) ethyl]amino]-1-phenylethanol monohydrochloride, 4.32 g of 2-aminothiazol-4-yl-acetic acid, 2.64 g of concentrated hydrochloric acid and 120 mL of water, 5.76 g of 1-(3-dimethylaminopropyl)-3-ethylcarbodiimide monohydrochloride (EDC) was added at room temperature, and the mixture was stirred for one hour. A mixed solution of 2.40 g of sodium hydroxide and 40 mL of water was dropped in the reaction solution, thereby undergoing crystallization. A generated crystal was collected by filtration and washed with water, followed by drying in vacuo. There was thus obtained 9.93 g of the β-form crystal of (R)-2-(2-aminothiazol-4-yl)-4'-[2-[(2-hydroxy-2-phenylethyl)amino]ethyl]acetanilide.

EXAMPLE 2

Production of the β-form Crystal Through Wet Cake of the β-form Crystal

To a mixed solution of 13.50 kg of (R)-2-[[2-(4-aminophenyl)ethyl]amino]-1-phenylethanol monohydrochloride, 7.29 kg of 2-aminothiazol-4-yl-acetic acid, 4.46 kg of concentrated hydrochloric acid and 270 L of water, 9.73 kg of 1-(3-dimethylaminopropyl)-3-ethylcarbodiimide monohydrochloride (EDC) was added at 15° C., and the mixture was stirred for one hour. A mixed solution of 4.10 kg of sodium hydroxide and 110 L of water was dropped in the reaction solution, thereby undergoing crystallization. A generated crystal was collected by filtration and washed with water to obtain 26.2 kg of a wet cake of the β-form crystal of (R)-2-(2-aminothiazol-4-yl)-4'-[2-[(2-hydroxy-2-phenylethyl) amino]ethyl]acetanilide. This crystal was used for recrystallization as it was in the wet state.

26.2 kg of the wet cake of the β-form crystal was added with and dissolved in 180 L of water and 140 L of ethanol by heating at about 80° C., and an external temperature was set up at 20° C., thereby rapidly cooling the solution. A generated crystal was filtered and dried to obtain 15.40 kg of the β-form crystal of (R)-2-(2-aminothiazol-4-yl)-4'-[2-[(2-hydroxy-2-phenylethyl)amino]ethyl]acetanilide.

Figure 1:
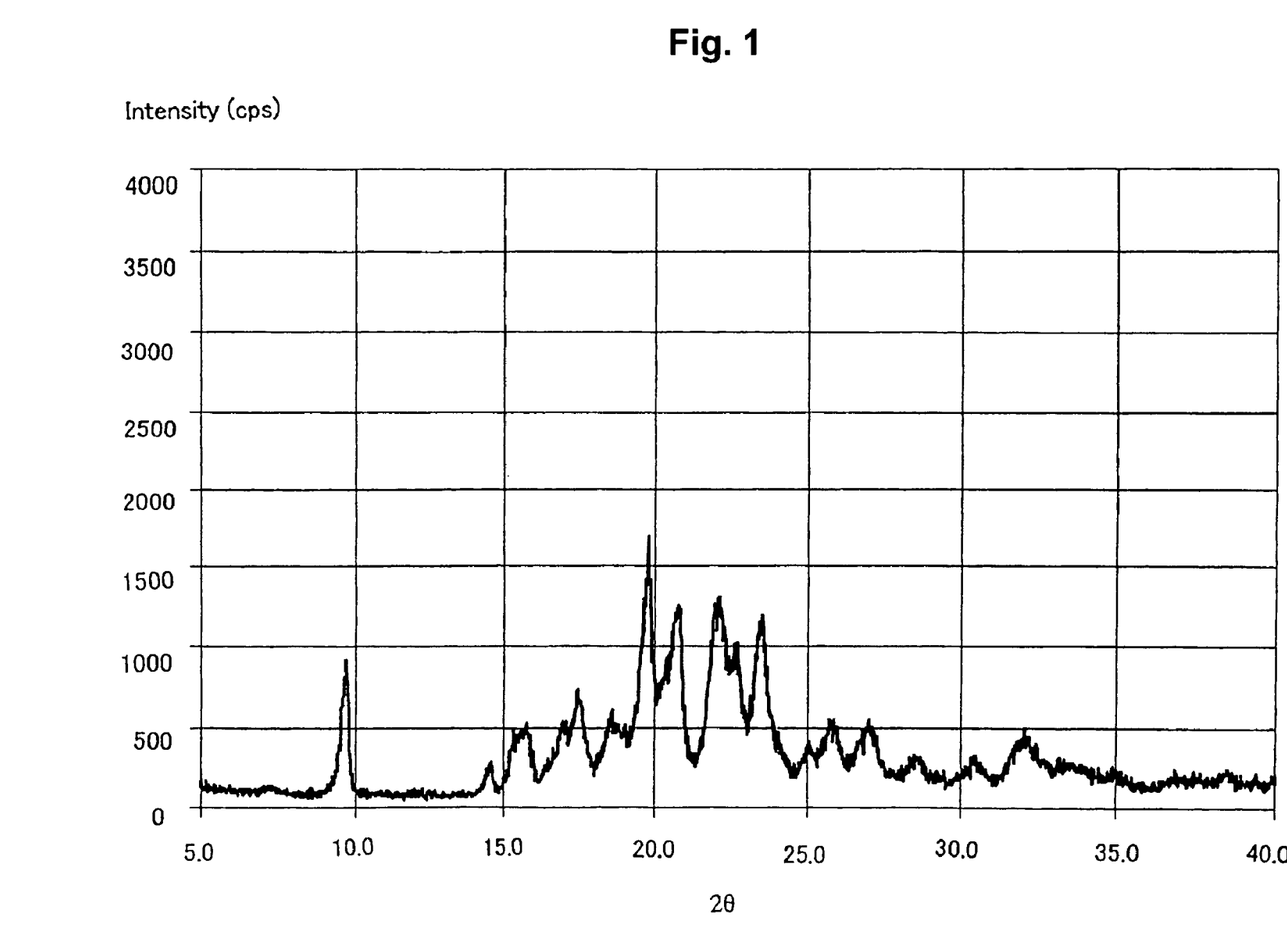
FIG. 1 is a powder X-ray diffraction diagram of the β-form crystal of (R)-2-(2-aminothiazol-4-yl)-4'-[2-[(2-hydroxy-2-phenylethyl)amino]ethyl]-acetanilide (crystal of the invention).
Figure 2:
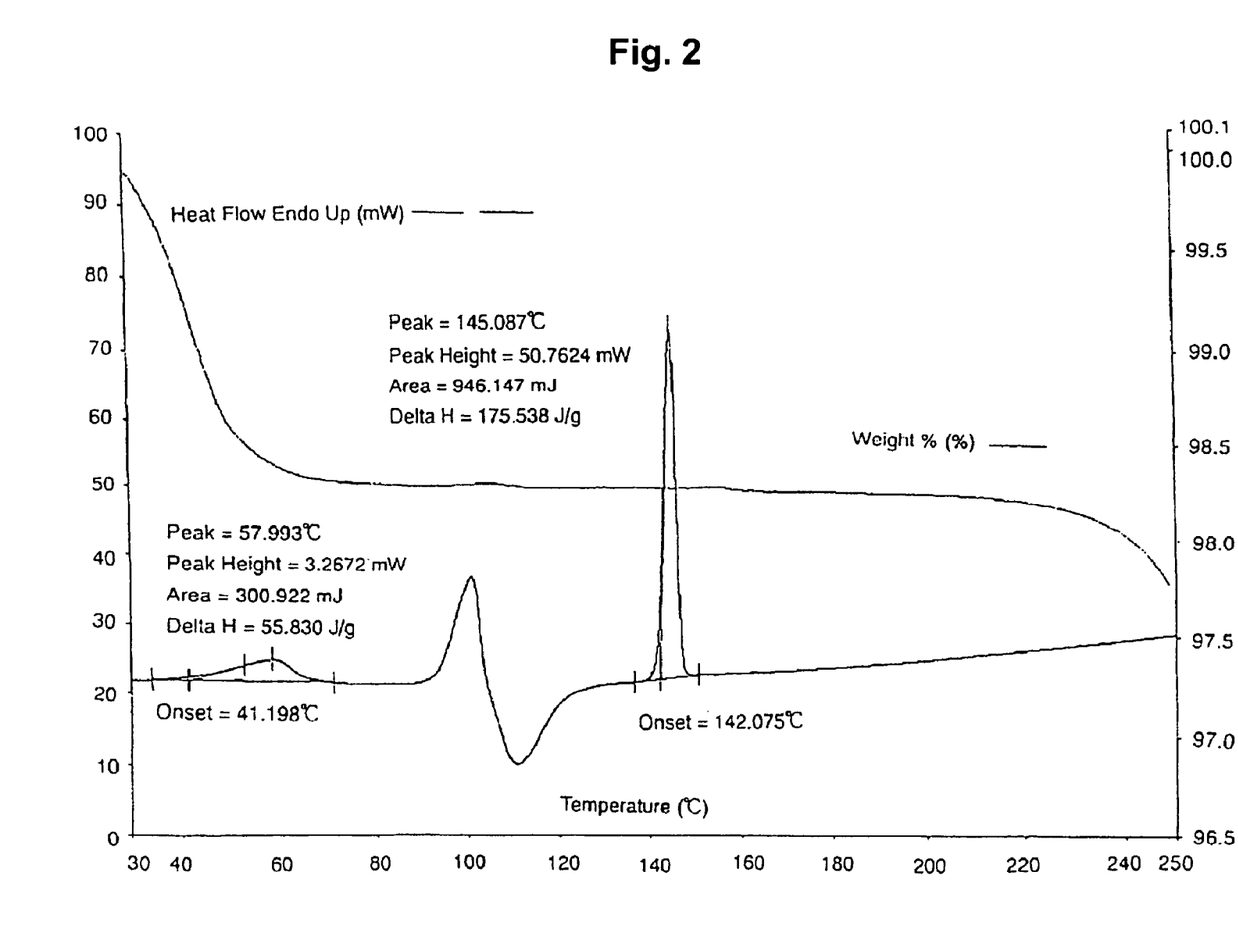
FIG. 2 is a thermal analysis diagram of the β-form crystal of (R)-2-(2-aminothiazol-4-yl)-4'-[2-[(2-hydroxy-2-phenylethyl)amino]ethyl]acetanilide (crystal of the invention).

Powder X-ray-diffraction diagram and thermal analysis diagram of the β-form crystal are shown in FIG. 1 and FIG. 2, respectively.
(Another Method) (Recrystallization Upon Seeding with the β-form Crystal):

A mixture of 7.54 g of the β-form crystal, 60 mL of ethanol and 90 mL of water was dissolved by heating and cooled, to which was then added 380 mg of the β-form crystal at 45° C. Thereafter, the mixture was stirred under ice cooling for 15 minutes. A crystal was filtered and dried to obtain 6.93 g of the β-form crystal.

EXAMPLE 3

Production of the α-form Crystal From the β-form Crystal

A mixture of 15.30 kg of the β-form crystal of (R)-2-(2-aminothiazol-4-yl)-4'-[2-[(2-hydroxy-2-phenylethyl)amino] ethyl]acetanilide, 180 L of water and 120 L of ethanol was dissolved by heating at about 80° C. and cooled, to which was then added 15.0 g of the α-form crystal at 50° C. Thereafter, the mixture was cooled to 20° C. A crystal was filtered and dried to obtain 14.24 kg of the α-form crystal of (R)-2-(2-aminothiazol-4-yl)-4'-[2-[(2-hydroxy-2-phenylethyl)amino] ethyl]acetanilide.

Figure 3:
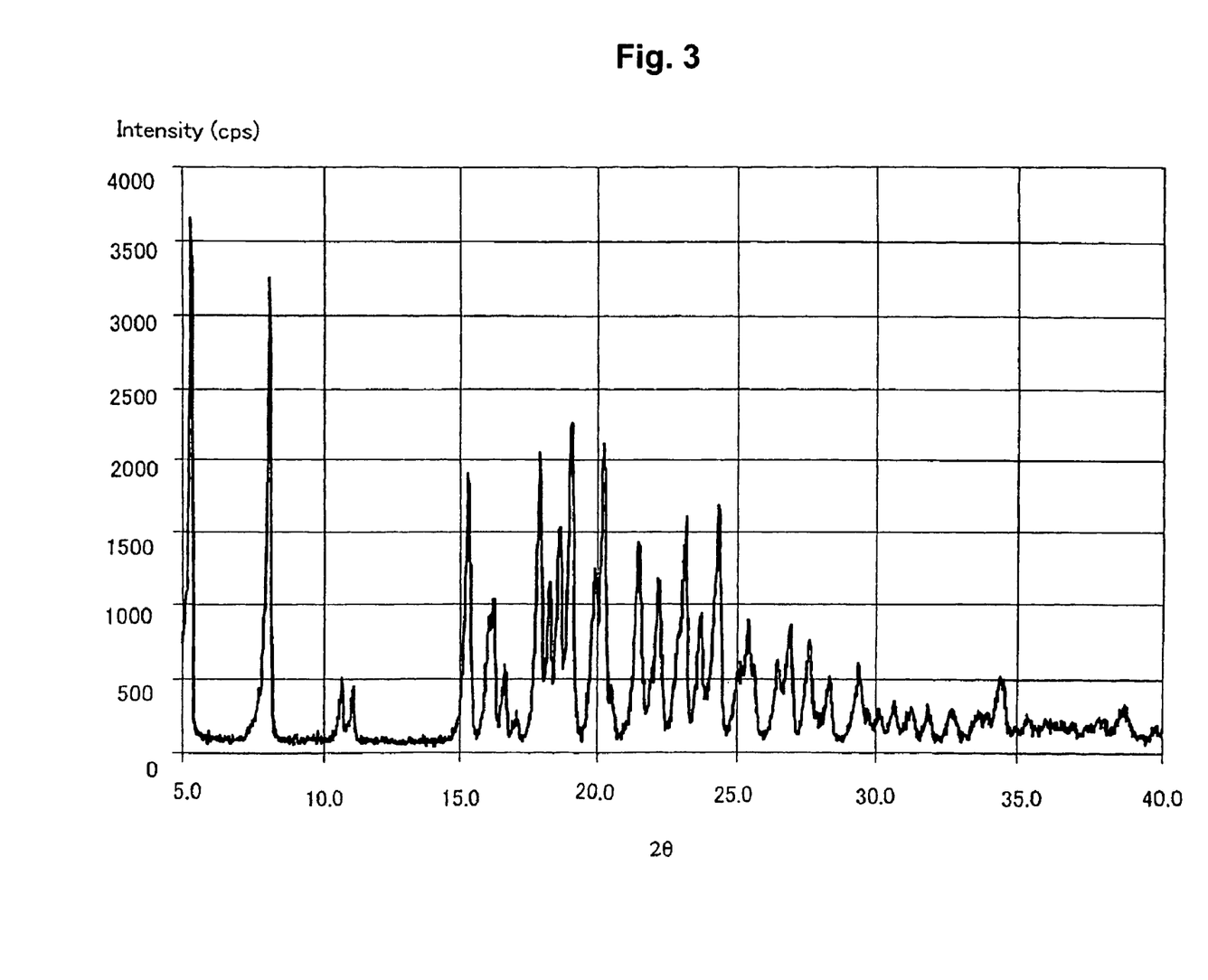
FIG. 3 is a powder X-ray diffraction diagram of the α-form crystal of (R)-2-(2-aminothiazol-4-yl)-4'-[2-[(2-hydroxy-2-phenylethyl)amino]ethyl]-acetanilide (crystal of the invention).

A powder X-ray diffraction diagram of the α-form crystal is shown in FIG. 3.

EXAMPLE 4

Production of the α-form Crystal from Wet Cake of the β-form Crystal

The same procedures as in Example 2 were followed to obtain 23.42 kg of a wet cake of the β-form crystal of (R)-2-(2-aminothiazol-4-yl)-4'-[2-[(2-hydroxy-2-phenylethyl) amino]ethyl]acetanilide from 6.66 kg of (R)-2-[[2-(4-aminophenyl)ethyl]amino]-1-phenylethanol monohydrochloride. This cake was added with and dissolved in 92 L of water and 76 L of ethanol by heating at about 80° C., and the solution was cooled at a rate of about 10° C. per hour, to which was then added 8.4 g of the α-form crystal at 55° C. Thereafter, the mixture was cooled to 20° C. A crystal was filtered and dried to obtain 6.56 kg of the α-form crystal of (R)-2-(2-aminothiazol-4-yl)-4'-[2-[(2-hydroxy-2-phenylethyl)amino]ethyl]acetanilide.

Figure 4:
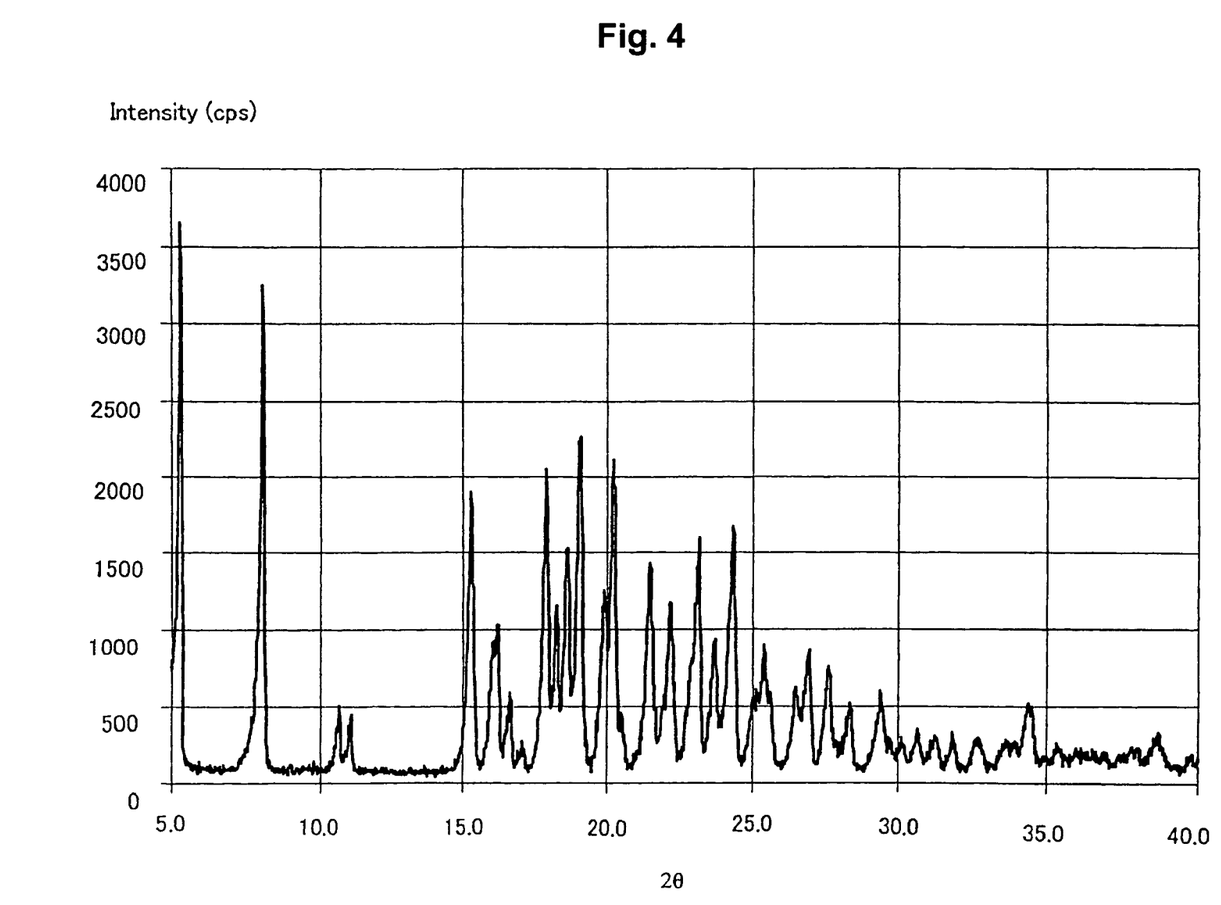
FIG. 4 is a powder X-ray diffraction diagram of the α-form crystal of (R)-2-(2-aminothiazol-4-yl)-4'-[2-[(2-hydroxy-2-phenylethyl)amino]ethyl]-acetanilide (crystal of the invention).
Figure 5:
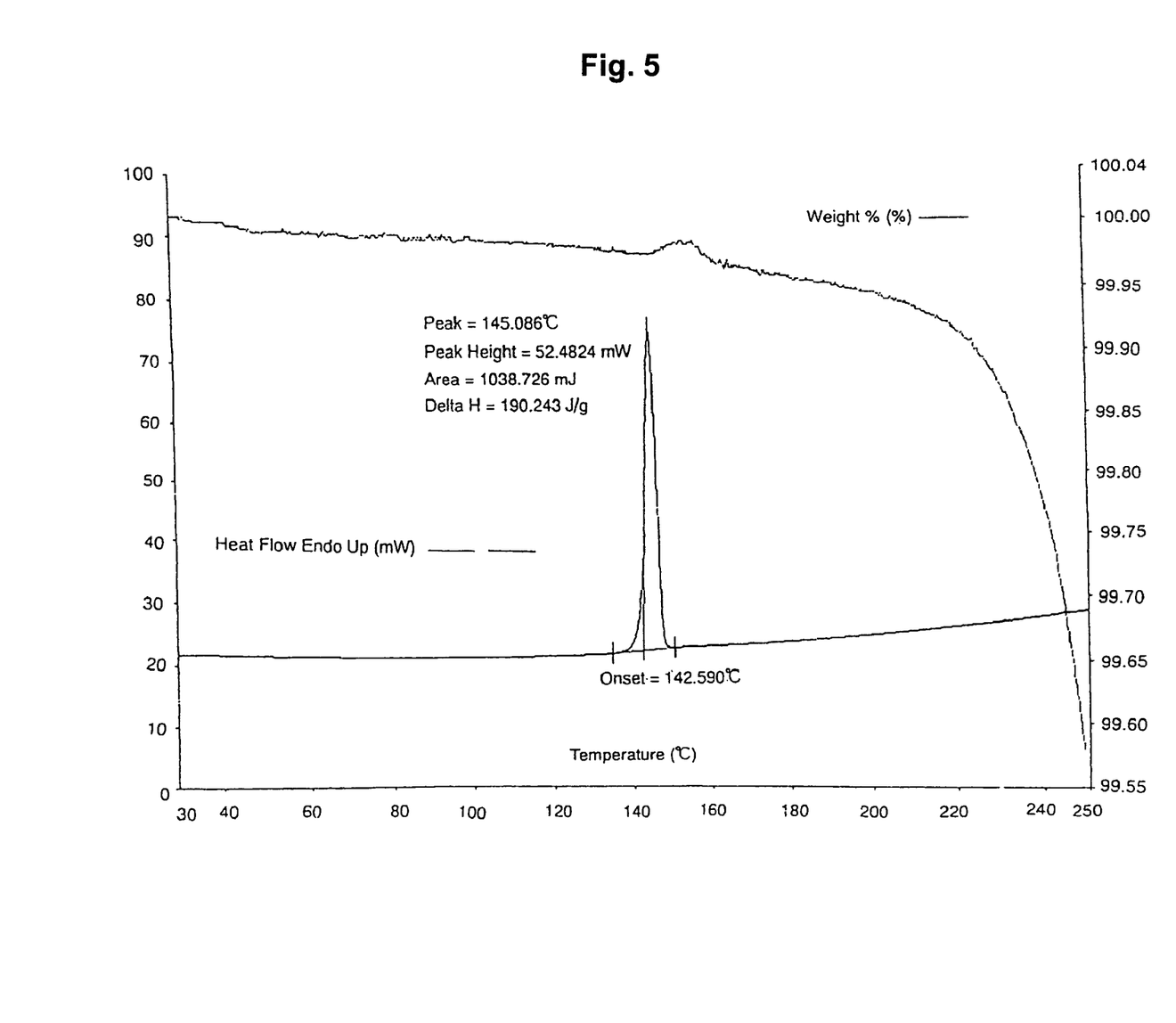
FIG. 5 is a thermal analysis diagram of the α-form crystal of (R)-2-(2-aminothiazol-4-yl)-4'-[2-[(2-hydroxy-2-phenylethyl)amino]ethyl]acetanilide (crystal of the invention).

Powder X-ray diffraction diagram and thermal analysis diagram of the α-form crystal are shown in FIG. 4 and FIG. 5, respectively.

$^1$H-NMR (DMSO-d$_6$, 500 MHz) δ (ppm)=1.60 (1H, s), 2.59 to 2.66 (4H, m), 2.68 to 2.80 (2H, m), 3.45 (2H, s), 4.59 (1H, br), 5.21 (1H, br), 6.30 (1H, s), 6.89 (2H, s), 7.11 (2H, d, J=8.5 Hz), 7.19 to 7.23 (1H, m), 7.27 to 7.33, (4H, m), 7.49 (2H, d, J=8.5 Hz), 9.99 (1H, s). FAB-MS m/z: 397 (M+H)$^+$.

COMPARATIVE REFERENTIAL EXAMPLE

Production of dihydrochloride 20.0 g of (R)-2-(2-aminothiazol-4-yl)-4'-[2-[(2-hydroxy-2-phenylethyl)amino]ethyl]acetanilide was dissolved in 1,4-dioxane, to which was then added 8.41 mL of concentrated hydrochloric acid. A generated crystal was collected by filtration to obtain 25.0 g of (R)-2-(2-aminothiazol-4-yl)-4'-[2-[(2-hydroxy-2-phenylethyl)amino]ethyl]-acetanilide dihydrochloride.

Figure 6:
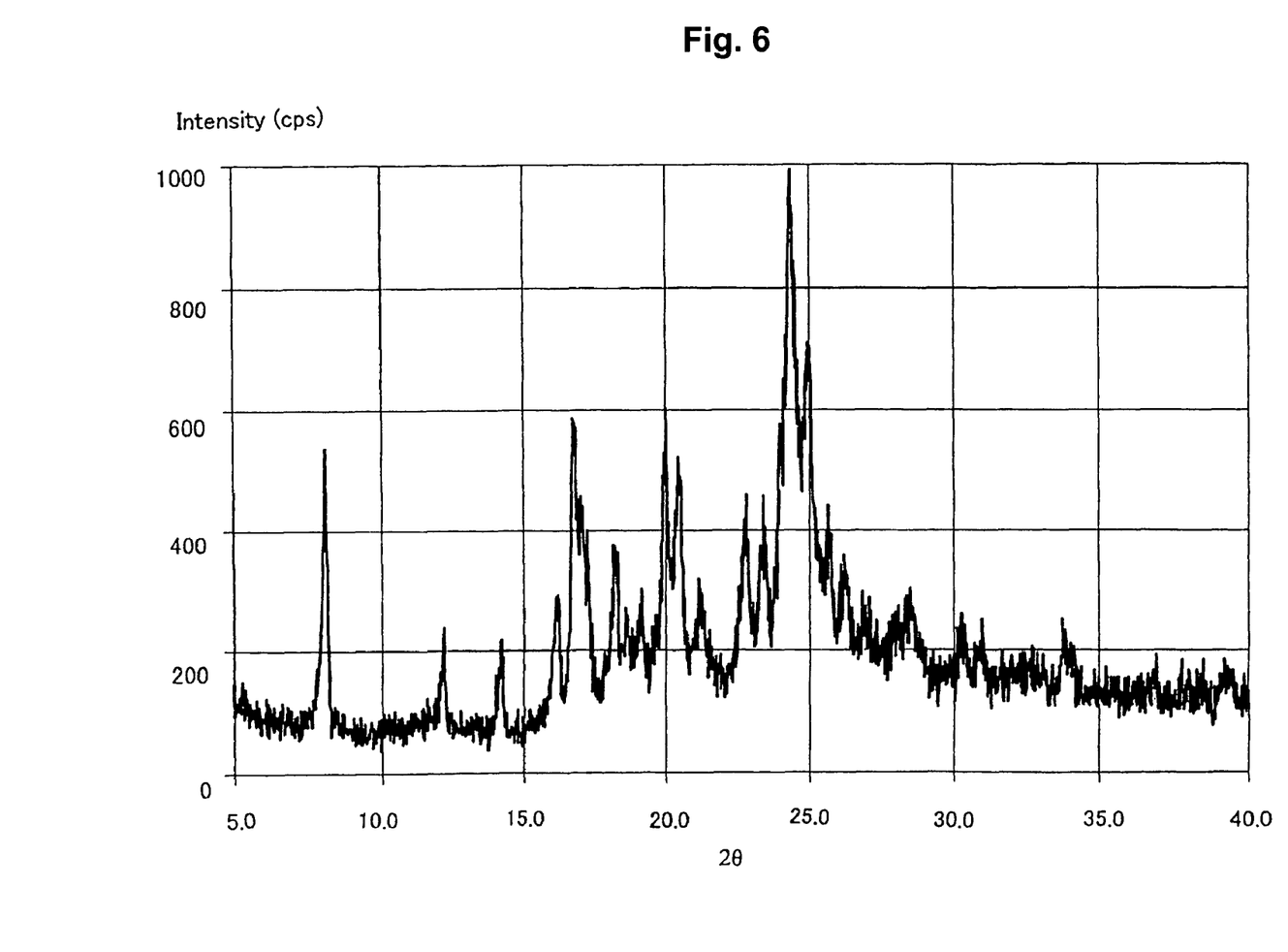
FIG. 6 is a powder X-ray diffraction diagram of the crystal of (R)-2-(2-aminothiazol-4-yl)-4'-[2-[(2-hydroxy-2-phenylethyl)amino]ethyl]acetanilide dihydrochloride.

A powder X-ray diffraction diagram of the dihydrochloride crystal is shown in FIG. 6.

$^1$H-NMR (DMSO-d$_6$, 400 MHz) δ (ppm)=2.90 to 3.08 (3H, m), 3.10 to 3.21 (3H, m), 3.75 (2H, s), 4.99 to 5.03 (1H, m), 6.69 (1H, s), 7.20 (2H, d, J=8.8 Hz), 7.28 to 7.43 (5H, m), 7.59 (2H, d, J=8.8 Hz), 8.94 (1H, brs), 9.17 (2H, br), 9.40 (1H, brs). FAB-MS m/z: 397 (M+H)$^+$.

INDUSTRIAL APPLICABILITY

The α-form crystal of the invention does not exhibit hygroscopicity and is stable, and therefore, can be used as a medicine and is useful as a medicine. Though the β-form crystal of the invention exhibits weak hygroscopicity, it is stable and useful as a production intermediate of the α-form crystal. Also, these crystals have both an insulin secretion promoting action and an insulin sensitivity potentiating action and are useful for remedy of diabetes. The usefulness of these crystals as medicines has been ascertained by the following hygroscopicity test and hypoglycemic test.

1. Hygroscopicity Test:

The hygroscopicity was measured using VTI SGA-100 under the following conditions. Temperature: 25° C., measurement range: from 5 to 95% of relative humidity, measurement interval: 5% of relative humidity.

Figure 7:
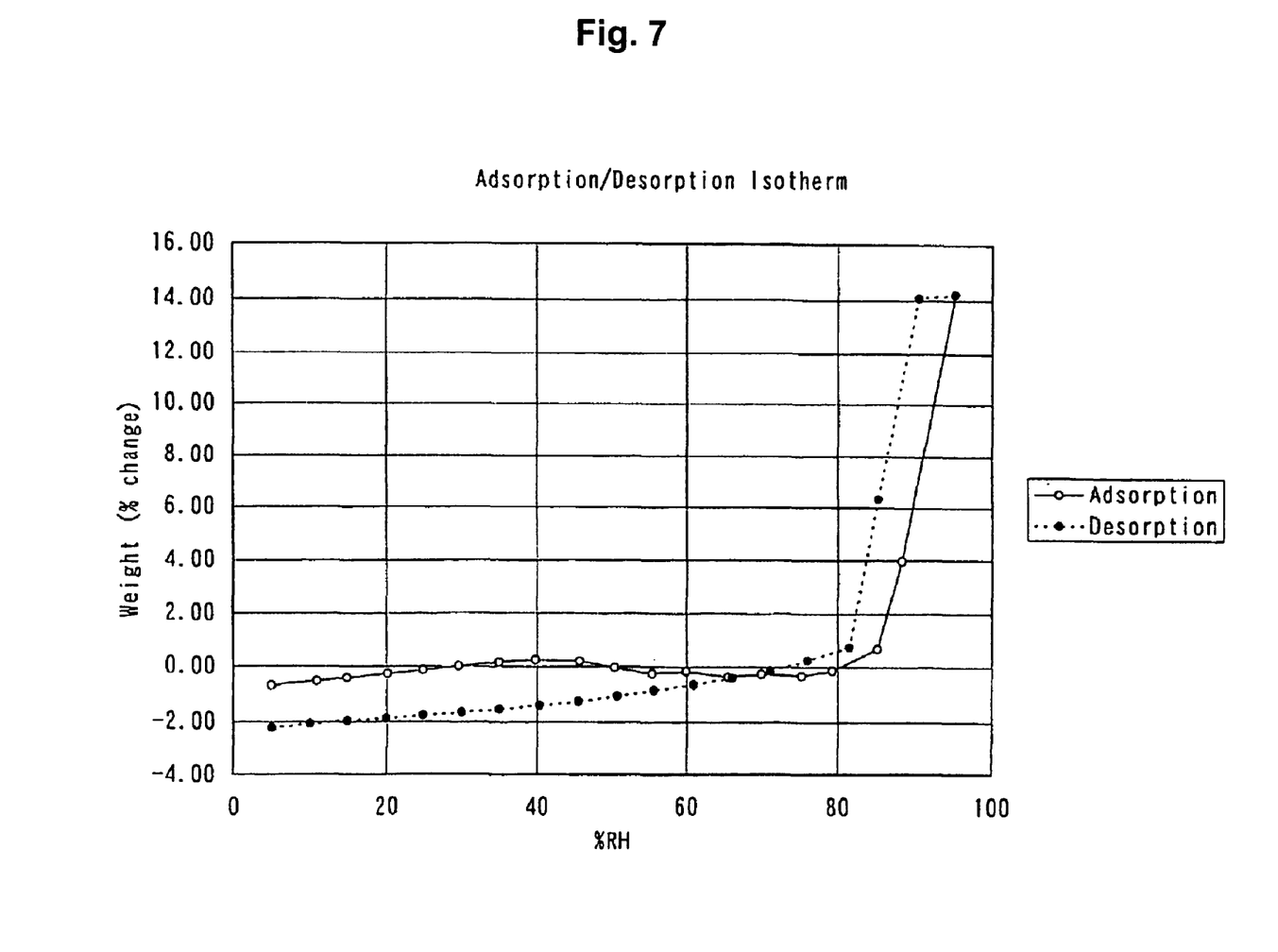
FIG. 7 is a hygroscopicity curve diagram of the crystal of (R)-2-(2-aminothiazol-4-yl)-4'-[2-[(2-hydroxy-2-phenylethyl)amino]ethyl]acetanilide dihydrochloride.
Figure 8:
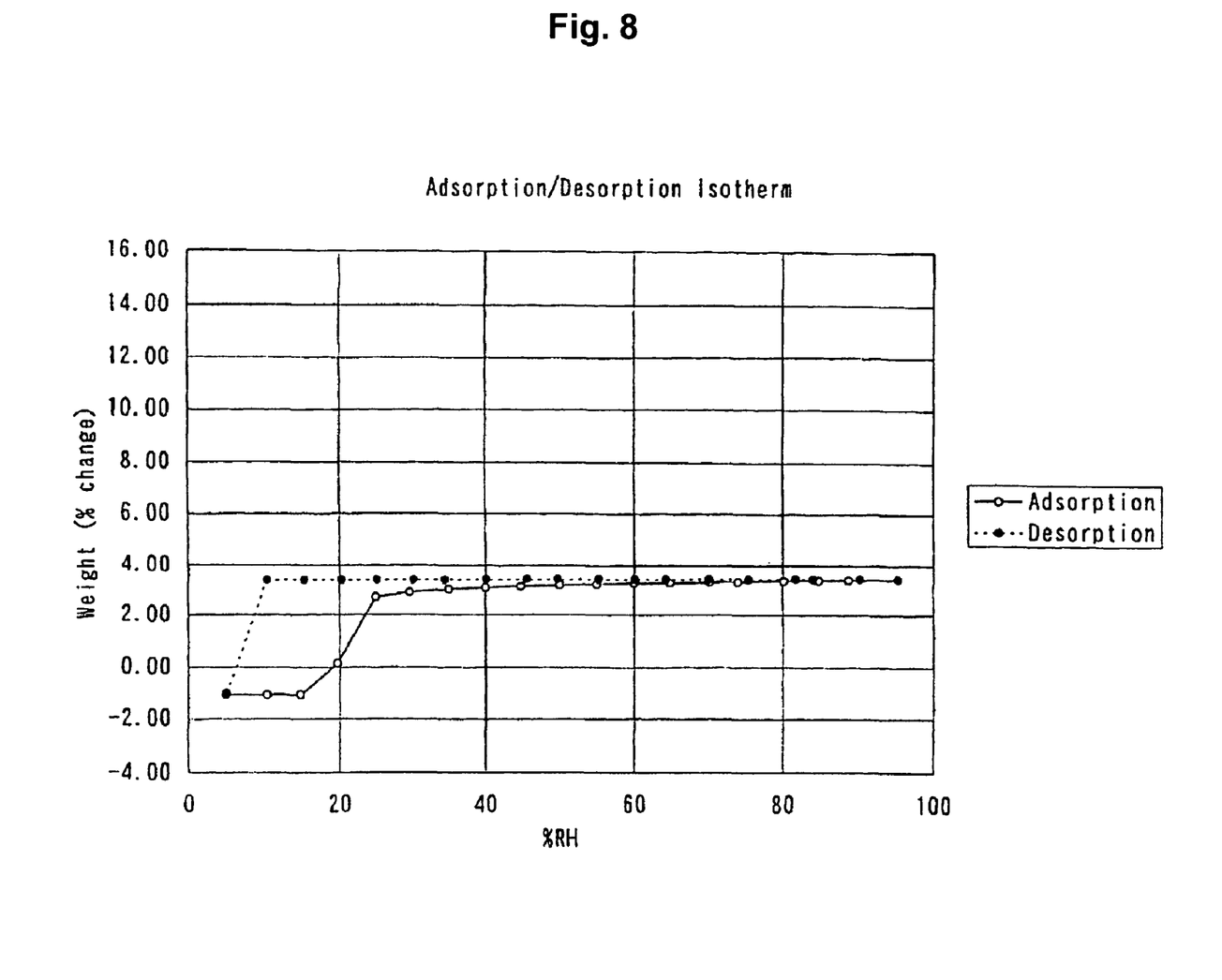
FIG. 8 is a hygroscopicity curve diagram of the β-form crystal of (R)-2-(2-aminothiazol-4-yl)-4'-[2-[(2-hydroxy-2-phenylethyl)amino]ethyl]acetanilide (crystal of the invention).
Figure 9:
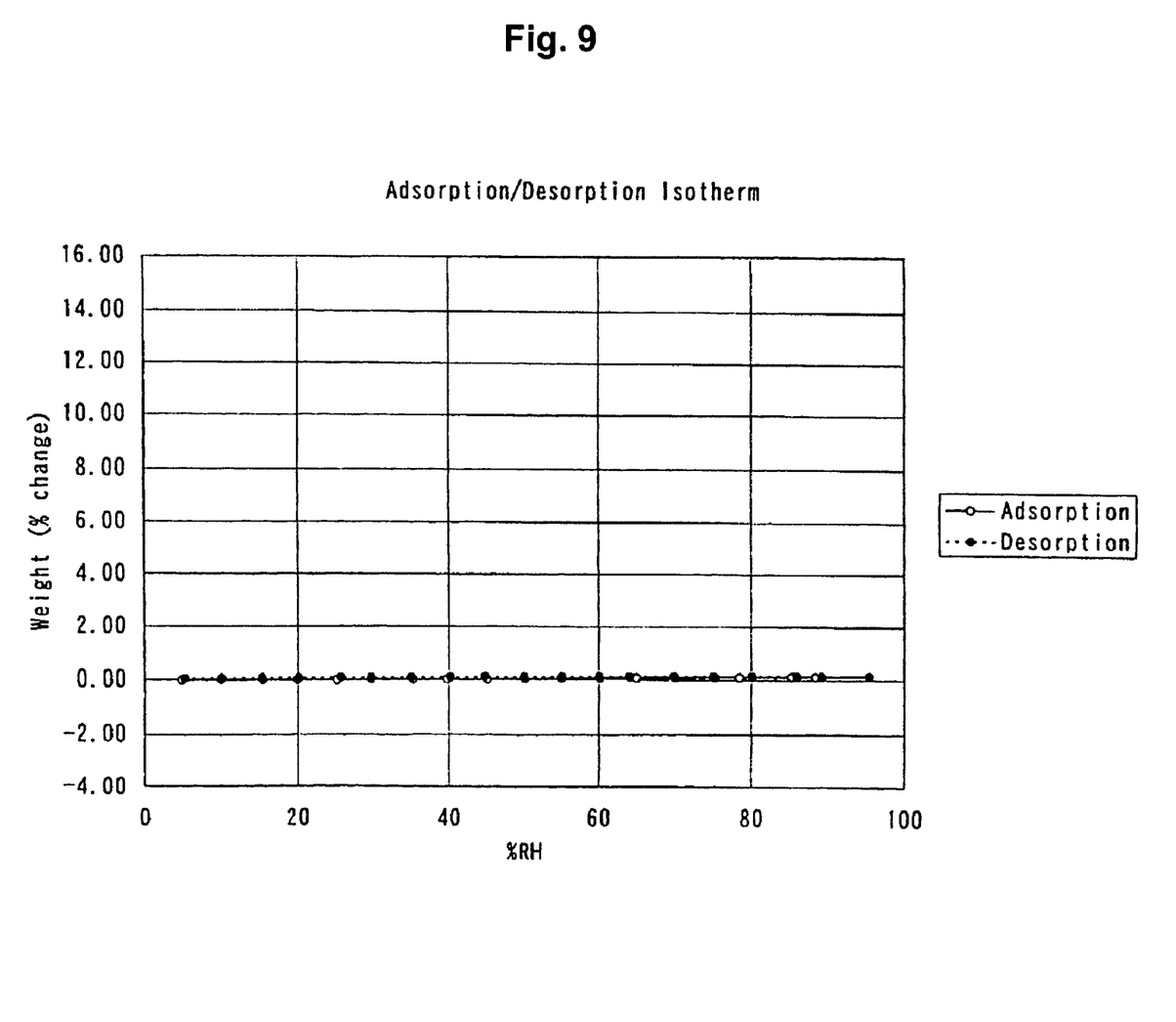
FIG. 9 is a hygroscopicity curve diagram of the α-form crystal of (R)-2-(2-aminothiazol-4-yl)-4'-[2-[(2-hydroxy-2-phenylethyl)amino]ethyl]acetanilide (crystal of the invention).

As a result, the crystal of (R)-2-(2-aminothiazol-1-4-yl)-4'-[2-[(2-hydroxy-2-phenylethyl)amino]ethyl]-acetanilide dihydrochloride exhibited a rapid increase in the weight from a relative humidity of about 80%, held moisture of about 14% at a relative humidity of 90%, and exhibited strong hygroscopicity (see FIG. 7). On the other hand, the α-form crystal of the invention had a moisture-holding amount of not more than 0.2% over the entire range of relative humidity from 5% to 95% and did not exhibit hygroscopicity (see FIG. 9). Also, in the β-form crystal, an increase in the weight was observed from a relative humidity of about 20%, and it held moisture of about 3% and exhibited weak hygroscopicity (see FIG. 8).

The foregoing crystal of (R)-2-(2-aminothiazol-4-yl)-4'-[2-[(2-hydroxy-2-phenylethyl)amino]ethyl]-acetanilide dihydrochloride exhibits strong hygroscopicity, and the physical and chemical nature and physical properties of the crystal vary and are unstable. On the other hand, the α-form crystal of the invention does not exhibit hygroscopicity and is excellent in stability, and therefore, is suitable as a starting material for the production of medicines. Though the "β-form crystal" has weak hygroscopicity, it is a metastable-form crystal and can be used as a medicine.

2. Hypoglycemic Test in kk Mice (Insulin Resistance Model: Obesity and Hyperglycemia)

Male kk mice (blood glucose level: 200 mg/dL or more) were measured for blood glucose level under feeding and then randomly classified into groups. The drug to be tested was compulsorily orally administered once daily for 7 days, and the blood glucose level after 15 to 18 hours from the final administration was compared with that before the administration (n=6). The blood was collected from a tail vein of the mouse using a glass capillary (previously treated with heparin), a protein was removed therefrom, and the amount of glucose in the supernatant (mg/dL) was measured by colorimetric determination by means of the glucose oxidase method. Further, a dose by which the blood glucose level was reduced by 30% as compared with that before the administration of the drug to be tested was expressed as an ED$_{30}$ value.

As a result, the α-form crystal exhibited a strong activity such that the ED$_{30}$ value in the oral administration was not more than 3.5 mg/kg/day.

3. Usefulness of the β-form Crystal as a Production Intermediate:

The β-form crystal is also useful as a production intermediate of the α-form crystal. The β-form crystal can be surely and simply obtained by quenching in the industrial production. Since the β-form crystal has high solubility in a recrystallization solvent (37% to 50% ethanol aqueous solution) as compared with the α-form crystal, the α-form crystal can be easily obtained by recrystallization of the β-form crystal.

In the drawings, "Intensity" stands for the intensity; "Temperature" stands for the temperature; "Heat Flow Endo Up" stands for the heat absorption; "Weight" stands for the weight; "Adsorption" stands for the adsorption; "Desorption" stands for the desorption; "Isotherm" stands for the curve; and "RH" stands for the relative humidity, respectively.

The invention claimed is:

1. A solid pharmaceutical composition comprising the α-form crystal of (R)-2-(2-aminothiazol-4-yl)-4'-[2-[(2-hydroxy-2-phenylethyl)amino]ethyl]acetanilide and a pharmaceutically acceptable carrier.

2. A method of treating diabetes in a patient in need thereof, comprising administering to the patient a solid pharmaceutical composition comprising the α-form crystal of (R)-2-(2-aminothiazol-4-yl)-4'-[2-[(2-hydroxy-2-phenylethyl)amino]ethyl]acetanilide and a pharmaceutically acceptable carrier.

3. A solid pharmaceutical composition comprising the β-form crystal of (R)-2-(2-aminothiazol-4-yl)-4'-[2-[(2-hydroxy-2-phenylethyl)amino]ethyl]acetanilide and a pharmaceutically acceptable carrier.

4. A method of treating diabetes in a patient in need thereof, comprising administering to the patient a solid pharmaceutical composition comprising the β-form crystal of (R)-2-(2-aminothiazol-4-yl)-4'-[2-[(2-hydroxy-2-phenylethyl)amino]ethyl]acetanilide and a pharmaceutically acceptable carrier.

5. The pharmaceutical composition of claim 1, wherein the pharmaceutically acceptable carrier is selected from a group consisting of lactose, mannitol, glucose, hydroxypropyl cellulose, microcrystalline cellulose, starch, polyvinylpyrolidone, and magnesium metasilicate aluminate.

6. The method of claim 2, wherein the pharmaceutically acceptable carrier is selected from a group consisting of lactose, mannitol, glucose, hydroxypropyl cellulose, microcrystalline cellulose, starch, polyvinylpyrolidone, and magnesium metasilicate aluminate.

7. The pharmaceutical composition of claim 3, wherein the pharmaceutically acceptable carrier is selected from a group consisting of lactose, mannitol, glucose, hydroxypropyl cellulose, microcrystalline cellulose, starch, polyvinylpyrolidone, and magnesium metasilicate aluminate.

8. The method of claim 4, wherein the pharmaceutically acceptable carrier is selected from a group consisting of lactose, mannitol, glucose, hydroxypropyl cellulose, microcrystalline cellulose, starch, polyvinylpyrolidone, and magnesium metasilicate aluminate.

9. The pharmaceutical composition of claim 1, wherein the α-form crystal of (R)-2-(2-aminothiazol-4-yl)-4'-[2-[(2-hydroxy-2-phenylethyl)amino]ethyl]acetanilide contains less than 0.2% of moisture.

10. The method of claim 2, wherein the α-form crystal of (R)-2-(2-aminothiazol-4-yl)-4'-[2-[(2-hydroxy-2-phenylethyl)amino]ethyl]acetanilide contains less than 0.2% of moisture.

11. The pharmaceutical composition of claim 3, wherein the β-form crystal of (R)-2-(2-aminothiazol-4-yl)-4'-[2-[(2-hydroxy-2-phenylethyl)amino]ethyl]acetanilide contains less than 3% of moisture.

12. The method of claim 4, wherein the β-form crystal of (R)-2-(2-aminothiazol-4-yl)-4'-[2-[(2-hydroxy-2-phenylethyl)amino]ethyl]acetanilide contains less than 3% of moisture.

13. The pharmaceutical composition of claim 1 in the form of a tablet, a pill, a capsule, granules, or powder.

14. The method of claim 2 wherein the solid pharmaceutical composition is in the form of a tablet, a pill, a capsule, granules, or powder.

15. The pharmaceutical composition of claim 3 in the form of a tablet, a pill, a capsule, granules, or powder.

16. The method of claim 4 wherein the solid pharmaceutical composition is in the form of a tablet, a pill, a capsule, granules, or powder.

* * * * *

UNITED STATES PATENT AND TRADEMARK OFFICE
CERTIFICATE OF CORRECTION

PATENT NO. : 7,982,049 B2  
APPLICATION NO. : 12/007653  
DATED : July 19, 2011  
INVENTOR(S) : Kawazoe et al.

Page 1 of 1

It is certified that error appears in the above-identified patent and that said Letters Patent is hereby corrected as shown below:

Title Page:

Item (63), "Continuation of application No. 10/494,018, filed on Apr. 29, 2004, now Pat. No. 7,342,117." should read --Continuation of application No. 10/494,018, filed as application No. PCT/JP02/11217 on Oct. 29, 2002, now Pat. No. 7,342,117.--

In the Specification:
COLUMN 1:

Lines 4-7, "This is a continuation of application Ser. No. 10/494,018, now U.S. Pat. No. 7,342,117, filed Apr. 29, 2004 and claims the benefit of PCT/JP02/11217 filed Oct. 20, 2002, all of which are incorporated herein by reference." should read --This application is a continuation of U.S. Application No. 10/494,018, which was the National Stage of International Application No. PCT/JP02/11217, filed Oct. 29, 2002, now U.S. Pat. No. 7,342,117, all of which are incorporated herein by reference.--

Signed and Sealed this  
Sixteenth Day of September, 2014

Michelle K. Lee  
*Deputy Director of the United States Patent and Trademark Office*